(12) United States Patent
Marie-Rose et al.

(10) Patent No.: US 8,927,762 B2
(45) Date of Patent: Jan. 6, 2015

(54) PRODUCTION OF OXYGENATED COMPOUNDS FROM CARBON MONOXIDE AND DIMETHYL CARBONATE

(71) Applicants: Stephane Marie-Rose, Sherbrooke (CA); Esteban Chornet, Sherbrooke (CA)

(72) Inventors: Stephane Marie-Rose, Sherbrooke (CA); Esteban Chornet, Sherbrooke (CA)

(73) Assignee: Enerkem, Inc., Montreal, Quebec (CA)

( * ) Notice: Subject to any disclaimer, the term of this patent is extended or adjusted under 35 U.S.C. 154(b) by 0 days.

(21) Appl. No.: 13/669,543

(22) Filed: Nov. 6, 2012

(65) Prior Publication Data

US 2013/0123533 A1    May 16, 2013

Related U.S. Application Data

(60) Provisional application No. 61/560,570, filed on Nov. 16, 2011.

(51) Int. Cl.
| | |
|---|---|
| *C07C 41/18* | (2006.01) |
| *C07C 41/01* | (2006.01) |
| *C07C 45/49* | (2006.01) |
| *C07C 67/36* | (2006.01) |

(52) U.S. Cl.
CPC .............. *C07C 67/36* (2013.01); *C07C 41/01* (2013.01); *C07C 45/49* (2013.01)
USPC .......................................... 560/232; 560/240

(58) Field of Classification Search
USPC .................................................. 560/232, 240
See application file for complete search history.

(56) References Cited

FOREIGN PATENT DOCUMENTS

| | | | | |
|---|---|---|---|---|
| WO | WO2008/132442 | | 11/2008 | |
| WO | WO-2008/132442 A1 * | 11/2008 | ............. | C07C 67/36 |
| WO | WO2008/132448 | | 11/2008 | |
| WO | WO2009/081099 | | 7/2009 | |
| WO | WO-2009/081099 A1 * | 7/2009 | ............. | C07C 51/12 |
| WO | WO2010/058149 | | 5/2010 | |
| WO | WO2010/130972 | | 11/2010 | |

* cited by examiner

*Primary Examiner* — Kamal Saeed
*Assistant Examiner* — Janet L Coppins
(74) *Attorney, Agent, or Firm* — Elliot M. Olstein; Raymond J. Lillie

(57) ABSTRACT

A method of producing at least one oxygenated compound, such as methyl acetate, dimethyl ether, and formaldehyde, by reacting dimethyl carbonate and carbon monoxide in the presence of a faujasite zeolite, zeolite Beta, Linde Type L (LTL) zeolite, or MCM-41 zeolite.

17 Claims, 3 Drawing Sheets

PRODUCTION OF OXYGENATED COMPOUNDS FROM CARBON MONOXIDE AND DIMETHYL CARBONATE

This Application claims priority based on provisional Application Ser. No. 61/560,570, filed Nov. 16, 2011, the contents of which are incorporated by reference in their entirety.

This invention relates to the production of oxygenated compounds, such as methyl acetate, dimethyl ether, and formaldehyde, from dimethyl carbonate and carbon monoxide. More particularly, this invention relates to the production of the above-mentioned oxygenated compounds by reacting dimethyl carbonate and carbon monoxide, which may be obtained from synthesis gas, in the presence of a faujasite zeolite, zeolite Beta, Linde Type L (LTL) zeolite, or MCM-41 zeolite.

In general, methyl acetate may be produced by reacting methanol with carbon monoxide in the presence of a catalyst and a co-catalyst, which may be methyl iodide or other halogenated compounds. An example of a catalyst and co-catalyst is a rhodium catalyst with a halide promoter, such as those described in published U.S. Patent Application No. U.S. 2009/0326080.

Alternatively, methyl acetate can be produced by reacting dimethyl carbonate with carbon monoxide in the presence of a mordenite zeolite catalyst Examples of mordenite zeolite catalysts which may be used to convert dimethyl carbonate to methyl acetate are disclosed in PCT Application No. WO2008/132442, and published U.S. Application Nos. US2010/0267985, US2010/0274045, US2010/0311567, US2010/0317888.

In accordance with an aspect of the present invention, there is provided a method of producing at least one oxygenated compound selected from the group consisting of methyl acetate, dimethyl ether, formaldehyde, and mixtures thereof. The method comprises reacting dimethyl carbonate with carbon monoxide under conditions which convert at least a portion of the dimethyl carbonate and at least a portion of the carbon monoxide to at least one oxygenated compound selected from the group consisting of methyl acetate, dimethyl ether, formaldehyde, and mixtures thereof.

The dimethyl carbonate and carbon monoxide are reacted in the presence of at least one zeolite catalyst selected from the group consisting of faujasite zeolites, zeolite Beta, Linde Type L (LTL) zeolite, MCM-41 zeolite, and mixtures thereof.

In a non-limiting embodiment, the at least one zeolite is a faujasite zeolite. In another non-limiting embodiment, the zeolite is zeolite Beta. In yet another non-limiting embodiment, the zeolite is LTL zeolite. In another non-limiting embodiment, the zeolite is MCM-41 zeolite.

Although the scope of the present invention is not to be limited to any theoretical reasoning, the faujasite, Linde Type L (LTL), zeolite Beta, and MCM-41 zeolites have increased amounts of active acid sites and/or increased surface areas as compared to other zeolites such as mordenite zeolites. For example, faujasite zeolites, LTL zeolite, and zeolite Beta have increased amounts of active acid sites, which provide for increased conversion of dimethyl carbonate to methyl acetate, dimethyl ether, and/or formaldehyde. In addition, faujasite zeolites, and LTL zeolite have "cage" type structures. Such "cage" type structures provide for greater diffusion of the reactants and the products into and through the pore channels of the zeolite, and provide for decreased coke formation and a longer duration of catalyst activity.

In addition, MCM-41 zeolite has a high surface area and a uniform mesoporous structure. Such high surface area and uniform mesoporous structure also provide for increased conversion of the dimethyl carbonate to the above-mentioned oxygenated compounds.

In a non-limiting embodiment, the above-mentioned zeolites are subjected to cation exchange with at least one cation. In a non-limiting embodiment, the zeolite is subjected to cation exchange with at least one cation selected from the group consisting of sodium, lithium, cesium, or mixtures thereof.

In another non-limiting embodiment, the above-mentioned zeolites may be mixed with alumina.

In a non-limiting embodiment, the at least one zeolite catalyst may be used as a support for at least one catalytic metal. Such catalytic metals include metals that contribute to the dissociative insertion of carbon monoxide or the non-dissociative insertion of carbon monoxide. In a non-limiting embodiment, the catalytic materials include, but are not limited to, transition metals of Group VII and Group VIII of the periodic table.

In a non-limiting embodiment, the at least one oxygenated compound is methyl acetate. In another non-limiting embodiment, the at least one oxygenated compound is dimethyl ether. In yet another non-limiting embodiment, the at least one oxygenated compound is formaldehyde.

In a further non-limiting embodiment, the at least one oxygenated compound is at least two of methyl acetate, dimethyl ether, and formaldehyde. In still another non-limiting embodiment, each of methyl acetate, dimethyl ether, and formaldehyde is produced by reacting dimethyl carbonate with carbon monoxide.

In another non-limiting embodiment, the carbon monoxide is obtained from synthesis gas. Thus, in a non-limiting embodiment, the dimethyl carbonate is contacted with synthesis gas, whereby the dimethyl carbonate is reacted with the carbon monoxide in the synthesis gas to produce at least one of methyl acetate, dimethyl ether, formaldehyde, or mixtures thereof.

In a non-limiting embodiment, the dimethyl carbonate is in the form of a gas when it is reacted with carbon monoxide gas to produce at least one of methyl acetate, dimethyl ether, and formaldehyde.

In a non-limiting embodiment, the dimethyl carbonate is reacted with the carbon monoxide at a temperature of from about 100° C. to about 600° C. In another non-limiting embodiment, the dimethyl carbonate is reacted with the carbon monoxide at a temperature of from about 100° C. to about 400° C.

In another non-limiting embodiment, the dimethyl carbonate and the carbon monoxide are reacted at a pressure of from about 14 psi to about 900 psi.

In a non-limiting embodiment, the dimethyl carbonate is reacted with the carbon monoxide at a molar ratio of dimethyl carbonate to carbon monoxide of from about 0.25:1 to about 10:1. In another non-limiting embodiment, the dimethyl carbonate is reacted with the carbon monoxide at a molar ratio of dimethyl carbonate to carbon monoxide of from about 0.25:1 to about 2:1. In another non-limiting embodiment, the dimethyl carbonate is reacted with the carbon monoxide at a molar ratio of dimethyl carbonate to carbon monoxide of from about 0.5:1 to about 1:1.

In a non-limiting embodiment, the dimethyl carbonate is reacted with the carbon monoxide at a gas hourly space velocity (GHSV), based on the amount of carbon monoxide present, of from about 100 $h^{-1}$ to about 60,000 $h^{-1}$.

The dimethyl carbonate may be reacted with the carbon monoxide in the presence of the catalyst hereinabove described in a suitable reactor known to those skilled in the art. Such reactors include, but are not limited to, fixed bed reactors, fluidized bed reactors, and three-phase reactors, i.e., reactors in which the dimethyl carbonate is reacted with carbon monoxide gas in the presence of the catalyst, wherein the catalyst is suspended in an inert liquid, such as an inert oil. In a non-limiting embodiment, the inert oil is a white mineral oil, such as, for example, Witco-70 or Drakeol.

In one non-limiting embodiment, the dimethyl carbonate is reacted with carbon monoxide in a three-phase reactor, wherein the zeolite catalyst hereinabove described is suspended in an inert liquid. In a non-limiting embodiment, the inert liquid is an inert oil.

In a non-limiting embodiment, the catalyst is in the form of a powder which is suspended in an inert high boiling oil, such as Witco-70 or Drakeol. In a non-limiting embodiment, the dimethyl carbonate is vaporized, and then mixed with carbon monoxide gas. A combined stream of vaporized dimethyl carbonate and carbon monoxide gas is dissolved in the oil, and the dissolved molecular species are reacted on the catalytic surfaces of the slurried catalyst. The reactor may be operated under the temperature and pressure conditions hereinabove described.

Although the scope of the present invention is not intended to be limited to any theoretical reasoning, the "three phase" reactor is used to adsorb heat released during the reaction and thus prevent potential "hot spots" due to overheating, and consequently, catalyst deactivation.

In another non-limiting embodiment, the dimethyl carbonate is reacted with the carbon monoxide in the presence of a fixed bed of the zeolite catalyst hereinabove described.

In another non-limiting embodiment, the dimethyl carbonate is reacted with the carbon monoxide in the presence of a fluidized bed of the zeolite catalyst hereinabove described.

In general, the catalyst has a particle size that is small enough for external mass transfer and internal diffusion resistance. In a non-limiting embodiment, the catalyst has a particle size of from about 20 microns to about 80 microns.

The invention now will be described with respect to the drawings, wherein.

Figure 1:
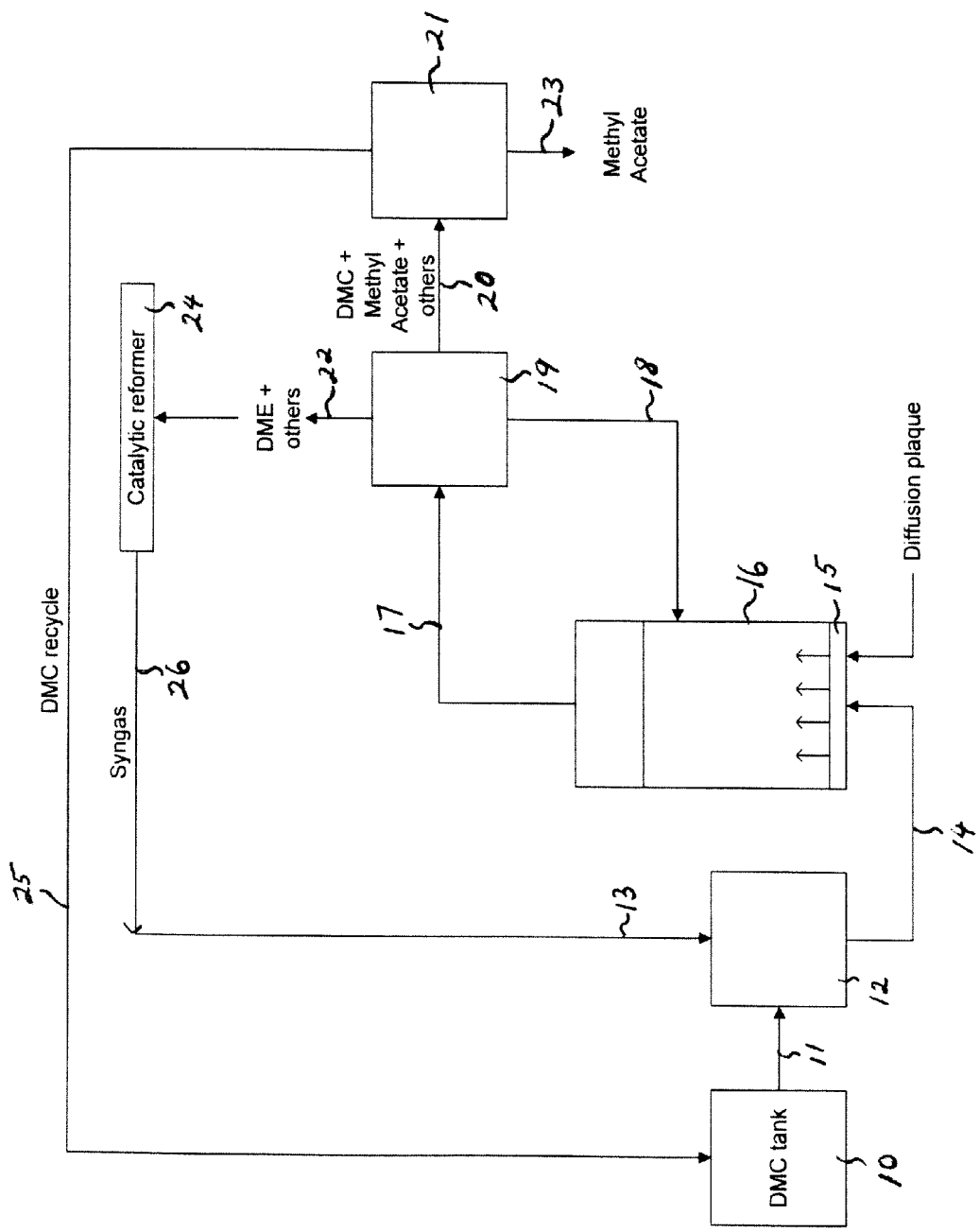
FIG. 1 is a schematic of a non-limiting embodiment of the process of the present invention.

Referring now to the drawings, as shown in FIG. 1, a liquid feed of dimethyl carbonate (DMC) in tank 10 is passed from line 11 to evaporator 12, wherein the dimethyl carbonate is vaporized into gaseous dimethyl carbonate. In general, the evaporator is operated at a temperature of from about 90° C. to about 200° C. As the dimethyl carbonate is evaporated in evaporator 12, synthesis gas is passed to evaporator 12 from line 13, and the vaporized dimethyl carbonate and the synthesis gas are mixed in evaporator 12. A combined stream of dimethyl carbonate and synthesis gas then is withdrawn from evaporator 12 through line 14, and then is passed through diffusion plaque 15, which is contained in reactor 16. Reactor 16 contains a zeolite catalyst as hereinabove described. Reactor 16 is a three-phase reactor in which the zeolite catalyst is suspended in an inert liquid, such as an inert oil.

In reactor 16, the vaporized dimethyl carbonate and the synthesis gas are reacted under conditions such as those hereinabove described such that the carbon monoxide in the synthesis gas is reacted with the dimethyl carbonate to form oxygenated compounds such as methyl acetate, dimethyl ether (DME), and formaldehyde. A product containing methyl acetate, dimethyl ether, formaldehyde, unreacted dimethyl carbonate, carbon dioxide, and unreacted synthesis gas, as well as a portion of the zeolite catalyst and a portion of the inert oil, is withdrawn from reactor 16 through line 17, and is passed to flash tower 19. Flash tower 19 is operated under conditions such that the methyl acetate and unreacted dimethyl carbonate are separated from the dimethyl ether, formaldehyde, carbon dioxide, and unreacted synthesis gas, as well as the portion of the zeolite catalyst and a portion of the inert oil. In general, the flash tower 19 is operated at a temperature of from about 5° C. to about 20° C., and at a pressure of from about 14 psi to about 900 psi.

Methyl acetate and unreacted dimethyl carbonate are withdrawn from flash tower 19 through line 20 and passed to distillation column 21. The portion of the zeolite catalyst and a portion of the inert oil are withdrawn from flash tower 19 through line 18 and recycled to reactor 16. In distillation column 21, a methyl acetate product is separated from the dimethyl carbonate and recovered through line 23. The dimethyl carbonate is withdrawn from distillation column 21 through line 25 as a liquid. The dimethyl carbonate in line 25 then is recycled to tank 10, wherein the recycled dimethyl carbonate is mixed with fresh dimethyl carbonate and is withdrawn from tank 10 through line 11 and passed to evaporator 12.

Dimethyl ether, formaldehyde, carbon dioxide, and unreacted synthesis gas are withdrawn from flash tower 19 through line 22, and passed to catalytic reformer 24. In catalytic reformer 24, the dimethyl ether, formaldehyde, and carbon dioxide, which are passed to catalytic reformer 24, are subjected to catalytic reforming conditions in order to produce additional synthesis gas. The reaction of dimethyl ether, formaldehyde, and carbon dioxide in catalytic reformer 24 is effected in the presence of an appropriate reforming catalyst. Such catalysts include, but are not limited to, nickel based catalysts and noble metal based catalysts. In general, the catalytic reformer is operated at a temperature of from about 300° C. to about 900° C., and at a pressure around atmospheric pressure. The synthesis gas then is withdrawn from catalytic reformer 24 through line 26. The synthesis gas in line 26 then is passed to line 13, and is recycled to evaporator 12.

Figure 2:
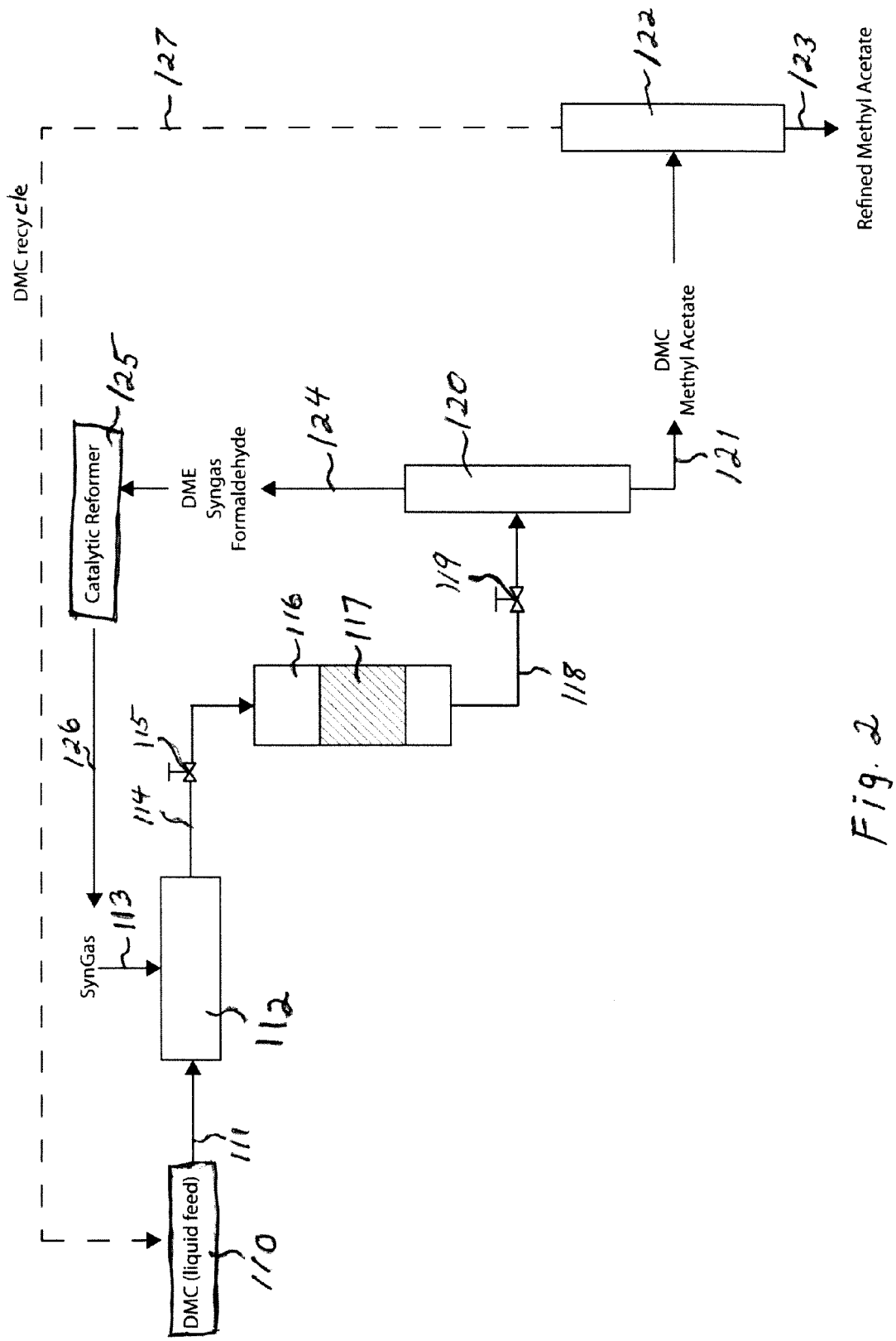
FIG. 2 is a schematic of another non-limiting embodiment of the process of the present invention.

In another non-limiting embodiment, as shown in FIG. 2, a liquid feed of dimethyl carbonate (DMC) in tank 110 is passed from line 111 to evaporator 112, wherein the dimethyl carbonate is vaporized into gaseous dimethyl carbonate. In general, the evaporator is operated at a temperature of from about 90° C. to about 200° C. As the dimethyl carbonate is evaporated in evaporator 112, synthesis gas is passed to evaporator 112 from line 113, and the vaporized dimethyl carbonate and the synthesis gas are mixed in evaporator 112. A combined stream of dimethyl carbonate and synthesis then is withdrawn from evaporator 112 through line 114, and valve 115, and is passed to reactor 116. Reactor 116 contains a fixed bed of the zeolite catalyst hereinabove described. The fixed bed of zeolite catalyst is shown schematically at 117.

In reactor 116, the vaporized dimethyl carbonate and the synthesis gas are reacted under conditions such as those hereinabove described such that the carbon monoxide in the synthesis gas is reacted with the dimethyl carbonate in the presence of the fixed bed 117 of zeolite catalyst to form oxygenated compounds such as methyl acetate, dimethyl ether (DME), and formaldehyde. A product containing methyl acetate, dimethyl ether, formaldehyde, unreacted dimethyl carbonate carbon dioxide, and unreacted synthesis gas is withdrawn from reactor 116 through line 118 and valve 119 and is passed to flash tower 120. Flash tower 120 is operated under conditions such that the methyl acetate and unreacted dimethyl carbonate are separated from the dimethyl ether, formaldehyde, carbon dioxide, and unreacted synthesis gas. In general, the flash tower 120 is operated at a temperature of from about 5° C. to about 20° C., and at a pressure of from about 14 psi to about 900 psi.

Methyl acetate and unreacted dimethyl carbonate are withdrawn from flash tower 120 through line 121 and passed to distillation column 122. In distillation column 122, a methyl acetate product is separated from the dimethyl carbonate and recovered through line 123. The dimethyl carbonate is withdrawn from distillation column 122 through line 127 as a liquid. The dimethyl carbonate is line 127 then is recycled to tank 110, wherein the recycled dimethyl carbonate is mixed with fresh dimethyl carbonate and is withdrawn from tank 110 through line 111 and passed to evaporator 112.

Dimethyl ether, formaldehyde, carbon dioxide, and unreacted synthesis gas are withdrawn from flash tower 120 through line 124 and passed to catalytic reformer 125. In catalytic reformer 125, the dimethyl ether, formaldehyde, and carbon dioxide, which are passed to catalytic reformer 125, are subjected to catalytic reforming conditions in order to produce additional synthesis gas. The reaction of dimethyl ether, formaldehyde, and carbon dioxide in catalytic reformer 125 is effected in the presence of an appropriate reforming catalyst. Such catalysts include, but are not limited to, nickel based catalysts and noble metal based catalysts. In general, the catalytic reformer is operated at a temperature of from about 300° C. to about 900° C., and at a pressure around atmospheric pressure. The synthesis gas then is withdrawn from catalytic reformer 125 through line 126. The synthesis gas in line 126 then is passed to line 113, and is recycled to evaporator 112.

Figure 3:
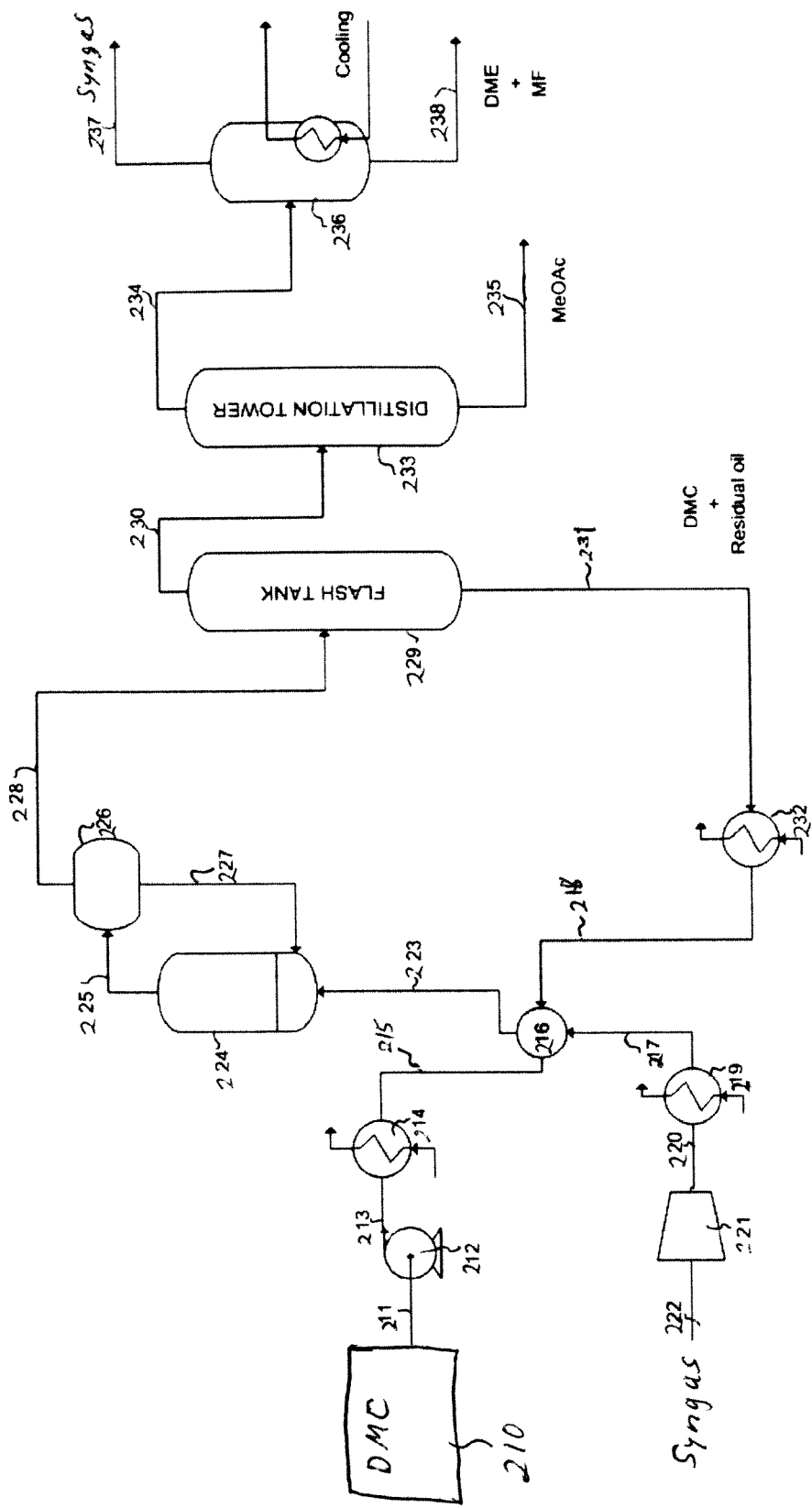
FIG. 3 is a schematic of yet another non-limiting embodiment of the process of the present invention.

In another non-limiting embodiment, as shown in FIG. 3, a liquid feed of dimethyl carbonate (DMC) in tank 210 is passed from line 211, through pump 212, and line 213 to evaporator 214, wherein the liquid dimethyl carbonate is vaporized. In general, evaporator 214 is operated at a temperature of from about 90° C. to about 200° C. The gaseous dimethyl carbonate is withdrawn from evaporator 214 through line 215, and is passed to mixing chamber 216. As the dimethyl carbonate is evaporated in evaporator 214, synthesis gas from line 222 is compressed in compressor 221. The compressed synthesis gas is withdrawn from compressor 221 through line 220, and is passed to preheater 219. The heated synthesis gas is withdrawn from preheater 219 though line 217 and is passed to mixing chamber 216. The vaporized dimethyl carbonate and synthesis gas are mixed in mixing chamber 216, and then withdrawn from mixing chamber 216 through line 223, and passed to "three phase" reactor 224. Reactor 224 contains a solid catalyst, such as a zeolite catalyst, which is suspended in an inert liquid, such as an inert oil.

In reactor 224, the vaporized dimethyl carbonate and the synthesis gas are reacted under conditions such as those hereinabove described such that the carbon monoxide in the synthesis gas is reacted with the dimethyl carbonate to from oxygenated compounds such as methyl acetate, dimethyl ether (DME), and formaldehyde. A product containing methyl acetate, dimethyl ether, formaldehyde, unreacted dimethyl carbonate, carbon dioxide, unreacted synthesis gas, a portion of the catalyst, and a portion of the inert oil, is withdrawn from reactor 224 through line 225, and is passed to flash tank 226. In general, flash tank 226 is operated at a temperature of from about 100° C. to about 230° C., and at a pressure of from about 14 psi to about 900 psi. Flash tank 226 thus is operated under conditions such that the methyl acetate, dimethyl ether, formaldehyde, unreacted dimethyl carbonate, carbon dioxide, and unreacted synthesis gas are separated from the portion of the catalyst and the portion of the inert oil. The portion of the inert oil and the portion of the catalyst are withdrawn from flash tank 226 through line 227 and are recycled to reactor 224.

The product containing methyl acetate, dimethyl ether, formaldehyde, unreacted dimethyl carbonate, carbon dioxide, and unreacted synthesis gas is withdrawn from flash tank 226 through line 228, and is passed to flash tank 229. In general, flash tank 229 is operated at a temperature of from about 5° C. to about 50° C. and at a pressure of from about 14 psi to about 900 psi. Thus, flash tank 229 is operated under conditions such that the methyl acetate, dimethyl ether, formaldehyde, carbon dioxide, and unreacted synthesis gas are separated from the any residual oil and unreacted dimethyl carbonate. The residual oil and unreacted dimethyl carbonate are withdrawn from flash tank 229 through line 231, passed through heater 232, and line 218, and then passed to mixing chamber 216.

Methyl acetate, dimethyl ether, formaldehyde, carbon dioxide, and unreacted synthesis gas are withdrawn from flash tank 229 through line 230, and passed to distillation column 233. In distillation column 233, the methyl acetate is separated from the dimethyl ether, formaldehyde, carbon dioxide, and unreacted synthesis gas, and is recovered through line 235.

Dimethyl ether, formaldehyde, carbon dioxide, and unreacted synthesis gas are withdrawn from distillation column 233 through line 234, and passed to cooling tower 236. In cooling tower 236, dimethyl ether and formaldehyde are separated from the carbon dioxide and unreacted synthesis gas. The dimethyl ether and formaldehyde are recovered from line 238. Carbon dioxide and unreacted synthesis gas are withdrawn from cooling tower 236 through line 237. The unreacted synthesis gas may, if desired, be separated from the carbon dioxide and recycled to compressor 221.

The disclosures of all patents and publications, including published patent applications, are incorporated herein by reference to the same extent as if each patent and publication were incorporated individually by reference.

It is to be understood, however, that the scope of the present invention is not to be limited to the specific embodiments described above. The invention may be practiced other than as particularly described and still be within the scope of the accompanying claims.

What is claimed is:

1. A method of producing at least one oxygenated compound selected from the group consisting of methyl acetate, dimethyl ether, formaldehyde, and mixtures thereof, comprising:
   reacting dimethyl carbonate with carbon monoxide under conditions which convert at least a portion of said dimethyl carbonate and at least a portion of said carbon monoxide to said at least one oxygenated compound, wherein said dimethyl carbonate and said carbon monoxide are reacted in the presence of at least one zeolite catalyst selected from the group consisting of faujasite zeolites, zeolite Beta, Linde Type L (LTL) zeolite, MCM-41, and mixtures thereof.

2. The method of claim 1 wherein said at least one zeolite is a faujasite zeolite.

3. The method of claim 1 wherein said at least one zeolite is zeolite Beta.

4. The method of claim 1 wherein said at least one zeolite is LTL zeolite.

5. The method of claim 1 wherein said at least one zeolite is MCM-41.

6. The method of claim 1 wherein said at least one oxygenated compound is methyl acetate.

7. The method of claim 1 wherein said carbon monoxide is obtained from synthesis gas.

8. The method of claim 1 wherein said dimethyl carbonate is reacted with said carbon monoxide at a temperature of from about 100° C. to about 600° C.

9. The method of claim 8 wherein said dimethyl carbonate is reacted with said carbon monoxide at a temperature of from about 100° C. to about 400° C.

10. The method of claim 1 wherein said dimethyl carbonate is reacted with said carbon monoxide at a pressure of from about 14 psi to about 900 psi.

11. The method of claim 1 wherein said dimethyl carbonate is reacted with said carbon monoxide at a molar ratio of dimethyl carbonate to carbon monoxide of from about 0.25:1 to about 10:1.

12. The method of claim 11 wherein said dimethyl carbonate is reacted with said carbon monoxide at a molar ratio of dimethyl carbonate to carbon monoxide of from about 0.25:1 to about 2:1.

13. The method of claim 12 wherein said dimethyl carbonate is reacted with said carbon monoxide at a molar ratio of dimethyl carbonate to carbon monoxide of from about 0.5:1 to about 1:1.

14. The method of claim 1 wherein said dimethyl carbonate is reacted with said carbon monoxide in a three-phase reactor, wherein said at least one zeolite catalyst is suspended in inert liquid.

15. The method of claim 14 wherein said inert liquid is an inert oil.

16. The method of claim 1 wherein said dimethyl carbonate is reacted with said carbon monoxide in a fixed bed reactor containing said at least one zeolite catalyst.

17. A method of producing methyl acetate, comprising:
(a) reacting dimethyl carbonate with synthesis gas in the presence of at least one zeolite catalyst, said synthesis gas containing carbon monoxide, under conditions which convert at least a portion of said dimethyl carbonate at least a portion of said carbon monoxide to a product comprising methyl acetate, dimethyl ether, formaldehyde, carbon dioxide, and unreacted synthesis gas, wherein said at least one zeolite catalyst is selected from the group consisting of faujasite zeolites, zeolite Beta, Linde Type L (LTL) zeolite, MCM-41, and mixtures thereof;
(b) separating said methyl acetate from said dimethyl ether, said formaldehyde, said carbon dioxide, and said unreacted synthesis gas;
(c) subjecting said dimethyl ether, said formaldehyde, said carbon dioxide, and said unreacted synthesis gas to catalytic reforming to produce additional synthesis gas; and
(d) reacting said unreacted synthesis gas and said additional synthesis gas of step (c) with said dimethyl carbonate in step (a).

* * * * *

UNITED STATES PATENT AND TRADEMARK OFFICE
CERTIFICATE OF CORRECTION

PATENT NO. : 8,927,762 B2  
APPLICATION NO. : 13/669543  
DATED : January 6, 2015  
INVENTOR(S) : Marie-Rose et al.

Page 1 of 1

It is certified that error appears in the above-identified patent and that said Letters Patent is hereby corrected as shown below:

On the title page item (71) and (72) line 3, after (CA) add -- Jean-Michel Lavoie, Sherbrooke, CA; David Lynch, Burlington, CT; --

Signed and Sealed this  
Thirty-first Day of March, 2015

Michelle K. Lee  
*Director of the United States Patent and Trademark Office*